United States Patent [19]

Bott et al.

[11] Patent Number: 4,863,641

[45] Date of Patent: Sep. 5, 1989

[54] PREPARATION OF ACYL HALIDES

[75] Inventors: Kaspar Bott, Mannheim; Erika Irnich, Bobenheim, both of Fed. Rep. of Germany

[73] Assignee: BASF Aktiengesellschaft, Ludwigshafen, Fed. Rep. of Germany

[21] Appl. No.: 226,834

[22] Filed: Aug. 1, 1988

[30] Foreign Application Priority Data

Jul. 31, 1987 [DE] Fed. Rep. of Germany ....... 3725428

[51] Int. Cl.$^4$ .................... C07C 51/58; C07C 53/46
[52] U.S. Cl. ................................................. 562/848
[58] Field of Search .................................... 260/544 A

[56] References Cited

U.S. PATENT DOCUMENTS 2,580,070 12/1951 Brooks et al. ................. 260/544 A

FOREIGN PATENT DOCUMENTS 3128445A 3/1983 Fed. Rep. of Germany .
2606772 5/1988 France .

Primary Examiner—Paul J. Killos
Attorney, Agent, or Firm—Keil & Weinkauf

[57] ABSTRACT

Preparation of acyl halides (I) by the reaction of halides of secondary or tertiary radicals derived from non-aromatic hydrocarbons (II) with carbon monoxide under elevated pressure in the presence of catalytic amounts of a Lewis acid, the catalyst consisting of a mixture of alkylaluminum halides corresponding to the general formula (III),

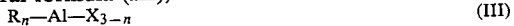

where R is an alkyl radical of from 1 to 8 carbon atoms, X is halogen, and n is an average whose valve is from 0.5 to 2.5.

2 Claims, No Drawings

PREPARATION OF ACYL HALIDES

The present invention relates to an improved process for the preparation of acyl halides by the reaction of halides of secondary or tertiary radicals derived from non-aromatic hydrocarbons with carbon monoxide under elevated pressure in the presence of catalytic amounts of a Lewis acid. From DE-OS 3 128 445 it is known that secondary or tertiary alkyl halides can be converted to the corresponding acid halides by treatment with carbon monoxide in the presence of aluminum chloride or aluminum chloride and ferric chloride as catalyst, and that equivalent amounts of the catalyst are not required. Good yields and selectivities are obtained especially in the presence of aluminum chloride, so that the use of this catalyst appears essential to the success of this process, at least when no other Brönsted or Lewis acd is added. However, using aluminum chloride is disadvantageous insofar as it is only slightly soluble in many of the solvents preferred for Friedel-Crafts syntheses, such as methylene chloride, chloroform, tetrachloroethylene, or trichlorobenzene. Solvents such as nitrobenzene or sulfolane, in which aluminum chloride is readily soluble, deactivate the catalyst.

For a continuous process, which is preferred in industry, it is important that the catalyst can be fed to the pressure reactor in solution, not as the solid, and of course its activity should not be diminished thereby. A general aim of the present invention was therefore to find a catalyst that does not suffer from the disadvantages described.

According to the earlier European Application No. 87 109 364.7 this aim is achieved by carrying out the carbonylation of halides of secondary or tertiary radicals derived from non-aromatic hydrocarbons with carbon monoxide in the presence of aluminum bromide alone or of aluminum bromide or chloride together with a halogenated hydrocarbon and the acid halide of a fatty acid of from 2 to 6 carbon atoms.

It is a particular aim of the present invention to further develop and improve on the principle of the process described in the earlier Patent Application.

We have found that this aim is achieved by a process for the preparation of acyl halides (I) by the reaction of halides of secondary or tertiary radicals derived from non-aromatic hydrocarbons (II) with carbon monoxide under elevated pressure in the presence of catalytic amounts of a Lewis acid if the catalyst consists of a mixture of alkylaluminum halides corresponding to the general formula (III),

$$R_n\text{—Al—}X_{3-n} \tag{III}$$

where R is an alkyl radical of from 1 to 8 carbon atoms, X is halogen, and n is an average whose value is from 0.5 to 2.5.

We have found further that this process is especially suitable for the preparation of acyl halides of the general formula (I′) from the corresponding halides (II′),

$$R^1R^2R^3C\text{—CO—Y} \tag{I′}$$

$$R^1R^2R^3C\text{—Y} \tag{II′}$$

where $R^1$ is hydrogen, alkyl, omega-haloalkyl, or cycloalkyl, $R^2$ and $R^3$ are each alkyl, omega-haloalkyl, or cycloalkyl or together form part of a ring of from 5 to 7 members, and Y is halogen.

The alkylaluminum halides are usually liquids. The n-alkylaluminum chlorides are commercially available and therefore preferred. They are generally supplied as solutions in chlorinated hydrocarbons or paraffins and are commonly mixtures whose average composition satisfies the general formula given above. They are readily soluble in aprotic organic solvents, and it is preferred to use them for the novel process as solutions in such solvents because this simplifies metering.

It is expedient to use from 0.005 mol to 0.05 mol, in particular from 0.01 mol to 0.03 mol, of alkylaluminum halide (III) per mole of halide (II).

Suitable starting substances (II) are above all those alkyl halides (II′) whose halogen atom Y is a fluorine, chlorine, or bromine atom. It is advantageous to employ bromides, especially advantageous to employ chlorides. The radical $R^1$ is hydrogen, branched or—preferably—unbranched alkyl or omega-haloalkyl—preferably chloroalkyl or bromoalkyl—, or cycloalkyl. The number of carbon atoms in the alkyl radical can be from 1 to 20, for instance, but is preferably from 1 to 10, especially from 1 to 5. The cycloalkyl group preferably has from 4 to 7 ring carbon atoms.

The following are examples of radicals $R^1$: methyl, ethyl, propyl, isopropyl, butyl, isobutyl, pentyl, isopentyl, hexyl, octyl, and dodecyl; chloromethyl, bromomethyl, and fluoromethyl; ethyl, propyl, butyl, pentyl, hexyl, heptyl, octyl, decyl, and dodecyl radicals terminally substituted by a fluorine, chlorine, or bromine atom; cyclobutyl, cyclopentyl, cyclohexyl, 4-methylcyclohexyl, and cycloheptyl.

The radicals $R^2$ and $R^3$ can be any of the radicals given above for $R^1$, other than hydrogen, but they can also be joined at one end, forming with the central carbon atom a ring, which may be bridged. In general the ring is five-, six-, or seven-membered. Examples of ring systems include cyclopentyl, cyclohexyl, cycloheptyl, bicyclo[2.2.1]heptyls, bicyclo[2.2.2]octyls, and bicyclo[3.2.1]octyls. The cycloalkyl radicals mentioned can also be substituted by alkyl radicals of from 1 to 4 carbon atoms.

The following are among the alkyl halides (II′) that are suitable starting substances: tert-butyl chloride and bromide, tert-pentyl chloride and bromide, 1,2-dichloro-2-methylpropane, 2-chloro-2-methylhexane, 2-bromo-2-methylhexane, 2-chloro-2-propylhexane, 1-chloro-1-methylcyclohexane, norbornyl chlorides, norbornyl bromides.

The reaction is carried out batchwise or, preferably, continuously in the known way. The carbon monoxide pressure is from about 50 bar to 700 bar, preferably from 200 bar to 600 bar, above all from 300 bar to 400 bar. The optimum reaction temperature depends on the starting substance (II) and the solvent; it is between $-20°$ C. and $30°$ C., preferably from $0°$ C. to $20°$ C., especially from $0°$ C. to $10°$ C.

Suitable solvents are liquid hydrocarbons, such as kerosenes, cycloalkanes, such as cyclohexane, and in particular chlorinated hydrocarbons, such as methylene chloride, dichloro-, trichloro-, and tetrachloroethanes, dichloro-, trichloro-, and tetrachloroethylenes, chlorobenzene, and dichloro- and trichlorobenzenes.

The ratio of the volume of solvent to the volume of the halide (II) can be from 5% to 200%; more advantageously it is from 10% to 30%.

In some cases the reaction proceeds faster in the presence of small quantities of a hydrogen halide, from about 0.1% to 1% of the mass of the halide (II). It is possible to pass gaseous hydrogen halide—preferably hydrogen chloride—through the halide (II) or the solvent before the reaction, but it is convenient to use crude halide (II), which usually still contains a certain amount of hydrogen halide.

It is advisable to add the catalyst (III) to the reaction mixture only under carbon monoxide under pressure, since otherwise undesirable side reactions can occur, for instance elimination of hydrogen halide from the halide (II).

When the reaction is complete the pressure can be lowered to atmospheric pressure, as is known processes, to allow separation of the product formed (I), unreacted starting substance (II), and any solvent that may be present from the catalyst. However, since it is possible for the acyl halide to decompose by reversal of the reaction by which it was formed, it is advisable to destroy the Lewis acid (III) before the pressure is lowered, for instance by adding the amide of a carboxylic acid. For this purpose it is preferable to use the amides of lower carboxylic acids, which can be separated from the reaction mixture easily, for example amides of carboxylic acids of from 1 to 5 carbon atoms, such as formamide, acetamide, propionamide, butyramide, or valeramide; particular preference is given to dimethylformamide.

Subsequent distillation of the reaction mixture is carried out in the usual way, so it is not necessary to go into this.

EXAMPLE

Under a carbon monoxide pressure of 250 bar and at a temperature of 5° C. 75 g (0.81 mol) of technical tert-butyl chloride containing (from its preparation) 1% by weight of hydrogen chloride was added to a solution of 2.25 g (0.018 mol) of ethylaluminum dichloride in 20 ml of methylene chloride. The carbonylation reaction was carried out over a period of 3 h by keeping the mixture at a temperature of from 5° C. to 7° C. under a carbon monoxide pressure of 300 bar.

Before the pressure was released 1.6 g (0.022 mol) of dimethylformamide was added to the reaction mixture in order to destroy the Lewis acid.

Gas-chromatographic analysis of the mixture after the pressure had been released showed that the yield of pivaloyl chloride was 82% and the selectivity 97%.

We claim:

1. A process for the preparation of acyl halides (I) by the reaction of halides of secondary or tertiary radicals derived from non-aromatic hydrocarbons (II) with carbon monoxide under elevated pressure in the presence of catalytic amounts of a Lewis acid, the catalyst consisting of a mixture of alkylaluminum halides corresponding to the general formula (III), $$R_n-Al-X_{3-n} \quad (III)$$

where R is an alkyl radical of from 1 to 8 carbon atoms, X is halogen, and n is an average whose value is from 0.5 to 2.5.

2. A process as claimed in claim 1 for the preparation of acyl halides of the general formula (I') from the corresponding halides (II'), $$R^1R^2R^3C-CO-Y \quad I'$$

$$R^1R^2R^3C-Y \quad II'$$

where $R^1$ is hydrogen, alkyl, omega-haloalkyl, or cycloalkyl, $R^2$ and $R^3$ are each alkyl, omega-haloalkyl, or cycloalkyl or together form part of a ring of from 5 to 7 members, and Y is halogen.

* * * * *